(12) United States Patent
Sengun et al.

(10) Patent No.: US 11,116,494 B2
(45) Date of Patent: Sep. 14, 2021

(54) COMPLIANT INSERTER FOR IMPLANTS

(71) Applicant: DePuy Synthes Products, Inc., Raynham, MA (US)

(72) Inventors: Mehmet Ziya Sengun, Canton, MA (US); Justin M. Piccirillo, Attleboro, MA (US); Gerome Miller, Randolph, MA (US); Arthur G. Stephen, Raynham, MA (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 330 days.

(21) Appl. No.: 16/242,094

(22) Filed: Jan. 8, 2019

(65) Prior Publication Data

US 2019/0133568 A1 May 9, 2019

Related U.S. Application Data

(62) Division of application No. 13/242,085, filed on Sep. 23, 2011, now Pat. No. 10,178,988.

(51) Int. Cl.
| | |
|---|---|
| *A61B 17/04* | (2006.01) |
| *B25B 23/10* | (2006.01) |
| *B25B 13/48* | (2006.01) |
| *A61B 17/00* | (2006.01) |
| *A61B 17/88* | (2006.01) |

(52) U.S. Cl.
CPC ...... *A61B 17/0401* (2013.01); *A61B 17/8875* (2013.01); *A61B 2017/00862* (2013.01); *A61B 2017/00946* (2013.01); *A61B 2017/0409* (2013.01); *B25B 13/481* (2013.01); *B25B 23/105* (2013.01); *B25B 23/106* (2013.01); *B25B 23/108* (2013.01)

(58) Field of Classification Search
CPC ........ A61B 17/8875; A61B 2017/0409; B25B 23/105; B25B 23/106; B25B 23/108; B25B 13/481
See application file for complete search history.

(56) References Cited

U.S. PATENT DOCUMENTS

| | | | |
|---|---|---|---|
| 2,086,270 | A | 7/1937 | Jenks |
| 2,814,322 | A | 11/1957 | Kupfrian |
| 3,675,312 | A | 7/1972 | Herman |
| 5,156,616 | A | 10/1992 | Meadows et al. |
| 5,380,334 | A | 1/1995 | Torrie et al. |
| 5,464,407 | A | 11/1995 | McGuire |

(Continued)

FOREIGN PATENT DOCUMENTS

| | | |
|---|---|---|
| JP | 06505888 | 7/1994 |
| JP | 2002516142 | 6/2002 |

(Continued)

*Primary Examiner* — Robert A Lynch

(57) ABSTRACT

An improved implant inserter, and method of using same, with an elongated, substantially rigid shaft having a proximal surface which is capable of receiving a driving force, and a substantially rigid tip portion having a distal end and a proximal end. At least the distal end of the tip portion is capable of being placed within an implant such as a suture anchor. The inserter further includes a compliant region disposed between the tip portion and the shaft which requires less lateral force to bend than the tip portion, at least when the tip portion has been placed within the implant.

3 Claims, 3 Drawing Sheets

(56) References Cited

U.S. PATENT DOCUMENTS

| | | |
|---|---|---|
| 5,690,676 A | 11/1997 | DiPoto |
| 5,797,918 A * | 8/1998 | McGuire ............... A61B 17/15 |
| | | 606/104 |
| 5,961,538 A | 10/1999 | Pedlick |
| 5,968,044 A | 10/1999 | Nicholson et al. |
| 6,464,706 B1 | 10/2002 | Winters |
| 6,527,795 B1 | 3/2003 | Lizardi |
| 6,813,975 B2 | 11/2004 | Kozak |
| 6,830,574 B2 | 12/2004 | Heckele et al. |
| 6,961,538 B2 | 11/2005 | Arsenault |
| 7,381,213 B2 | 6/2008 | Lizardi |
| 2002/0058945 A1 | 5/2002 | Steiner et al. |
| 2002/0133179 A1 | 9/2002 | McDevitt et al. |
| 2005/0033430 A1 | 2/2005 | Powers et al. |
| 2006/0247658 A1 | 11/2006 | Pond |
| 2007/0017954 A1 | 1/2007 | Dion |
| 2008/0147063 A1 | 6/2008 | Cauldwell |
| 2008/0188854 A1 | 8/2008 | Moser |
| 2008/0243136 A1 | 10/2008 | Prager et al. |
| 2009/0157123 A1 | 6/2009 | Appenzeller et al. |
| 2009/0192545 A1 | 7/2009 | Workman |
| 2010/0076502 A1 | 3/2010 | Guyer |
| 2010/0292704 A1 | 11/2010 | Stoffel |

FOREIGN PATENT DOCUMENTS

| | | |
|---|---|---|
| JP | 2002537007 | 11/2002 |
| JP | 2007501055 | 1/2007 |
| WO | WO 9008510 A1 | 8/1990 |

* cited by examiner

COMPLIANT INSERTER FOR IMPLANTS

CROSS REFERENCE TO RELATED APPLICATIONS

This application is a divisional of U.S. patent application Ser. No. 13/242,085, entitled COMPLIANT INSERTER FOR IMPLANTS, filed Sep. 23, 2011, now U.S. Pat. No. 10,178,988 which is incorporated herein by reference.

BACKGROUND OF THE INVENTION

1. Field of the Invention

The invention relates to tools for inserting implants into bone and more particularly to drivers for suture anchors.

2. Description of the Related Art

A common injury, especially among athletes, is the complete or partial detachment of tendons, ligaments or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors and tacks.

Arthroscopic tissue attachment is commonly practiced in shoulder rotator cuff and instability procedures. Typically, an anchor loaded with suture is fixated to bone using an inserter-type device. The suture is normally slidably attached to the anchor through an eyelet or around a post, such that a single length of suture has two free limbs. The suture limbs typically are carried along the exterior of the inserter, usually within a groove or other exterior channel, or within the interior of the inserter. After the anchor is inserted into the bone, one limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

Some anchor inserters are utilized to push an anchor into a pre-drilled hole in a bone, such as shown in U.S. Pat. No. 7,381,213 by Lizardi, while other inserters apply torque to a helically threaded anchor to rotate the anchor into a pre-formed hole, such as illustrated in U.S. Patent Publication No. 2008/0147063 by Cauldwell et al. Certain anchors are asymmetrical and require relatively small force for insertion, while other, symmetrical anchors must be driven at a higher forces to ensure sufficient fixation between the anchor and the bone. Some anchors benefit from internal support by a substantially rigid tip of an inserter while being driven into bone.

The tip of an implant driver typically is constructed of a hardened material which may be strong but brittle. In other words, the driver tip usually lacks ductility. Large strains imparted on a material may result in failure of the implant and/or the driver tip. Failure of the driver tip may result in breakage which must be retrieved from the patient. Strains may arise when an implant is being inserted at an off-axis angle into a hole in bone, or when the implant is partially or fully inserted and a laterally-directed load is applied to the driver handle.

One type of asymmetric, push-in anchor is disclosed by Pedlick et al. in U.S. Pat. No. 6,961,538. In one embodiment, an installation tool has a substantially rigid elongated rod with a somewhat flexible distal end that encourages a plow-like edge of a wedge-shaped anchor to dig into the wall of a pre-formed hole in bone. The installation tool does not appear to be capable of providing any internal support to the anchor during insertion.

Another type of asymmetric anchor is described by Lizardi in U.S. Pat. No. 6,527,795. A tapered anchor has a flared portion on its trailing end. An insertion tool may include a flexible portion that allows the tool to bend when pressure is exerted to generate a compressive force that is greater on one side of the anchor, which toggles or rotates the anchor.

A further consideration is having sufficient yet releasable attachment between the anchor and the inserter. Some systems rely on an interference fit, while others utilize a threaded engagement. A implant inserter device is described by Stoffel et al. in U.S. Patent Publication No. 2010/0292704 having an inner sleeve which collapses from an undeformed position to a deformed position to grip an implant.

It is therefore desirable to have an improved inserter which can apply sufficient insertion force to an implant without damaging the implant and without breakage.

SUMMARY OF THE INVENTION

An object of the present invention is to provide an improved inserter which concentrates bending forces in a localized region to control deformation and minimize breakage.

Another object of the present invention is to provide such an inserter which can generate internal support for an implant.

This invention features an implant inserter including an elongated, substantially rigid shaft having a proximal surface which is capable of receiving a driving force, and a substantially rigid tip portion having a distal end and a proximal end. At least the distal end of the tip portion is capable of being placed within an implant. The inserter further includes a compliant region disposed between the tip portion and the shaft which requires less lateral force to bend than the tip portion, at least when the tip portion has been placed within the implant.

In some embodiments, the tip portion is capable of providing internal support for the implant during insertion into bone, and the compliant region is formed of a material that is more malleable than that of the tip portion. In other embodiments, the compliant region includes a bellows-type structure with a plurality of convolutions or other variations in cross-sectional shape. In certain embodiments, the distal tip is capable of applying torque to the implant.

In some embodiments, the inserter further includes a distal-facing shoulder at the proximal end of the tip portion capable of engaging the proximal end of the implant. In certain embodiments, the compliant region has a smaller cross-section than that of the shoulder. In a number of embodiments, the inserter is placed within a package and sterilized, the sterilization occurring before, during or after being placed in the package. The implant such as a suture anchor is placed within the same package in some embodiments and in a different sterilizable package in other embodiments. The package maintains sterility of the inserter and of the implant if present.

In some embodiments, the inserter further includes at least one implant retention element carried by the tip, such as a laterally-extending projection formed on the tip. In one embodiment, the projection has a smooth distal leading edge and a sharply-defined transition at a trailing edge.

This invention may also be expressed as a combination including a suture anchor having a distal end and a proximal end, and defining a lumen open at the proximal end. The combination further includes an inserter with an elongated, substantially rigid shaft having a proximal surface which is capable of receiving a driving force, and a substantially rigid tip portion having a distal end and a proximal end. At least the distal end of the tip portion is capable of being placed within the lumen of the suture anchor to provide internal support for the suture anchor during insertion into bone. A distal-facing shoulder at the proximal end of the tip portion is capable of engaging the proximal end of the suture anchor. The inserter further includes a compliant region disposed between the shoulder and the shaft which requires less lateral force to bend than the tip portion, at least when the tip portion has been placed within the implant.

This invention may be further expressed as a method of inserting a suture anchor into bone, including selecting a suture anchor having a distal end and a proximal end, and defining a lumen open at the proximal end. The method further includes coupling the suture anchor to an inserter including an elongated, substantially rigid shaft having a proximal surface which is capable of receiving a driving force, a substantially rigid tip portion having a distal end and a proximal end, and at least the distal end capable of being placed within the lumen of the suture anchor to provide internal support for the suture anchor during insertion into bone, the inserter further including a distal-facing shoulder at the proximal end of the tip portion capable of engaging the proximal end of the suture anchor, and a compliant region disposed between the shoulder and the shaft which requires less lateral force to bend than the tip portion, at least when the tip portion has been placed within the suture anchor. The suture anchor is then driven into the bone.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by an implant inserter with an elongated, substantially rigid shaft having a proximal surface which is capable of receiving a driving force, and a substantially rigid tip portion having a distal end and a proximal end. The tip portion is capable of being placed within an implant. The inserter further includes a compliant region disposed between the tip portion and the shaft which requires less lateral force to bend than the tip portion, at least when the tip portion has been placed within the implant. The term "bend" includes elastic, plastic and irreversible deformations of the compliant region, but does not include fracture or other breakage thereof.

Figure 1:
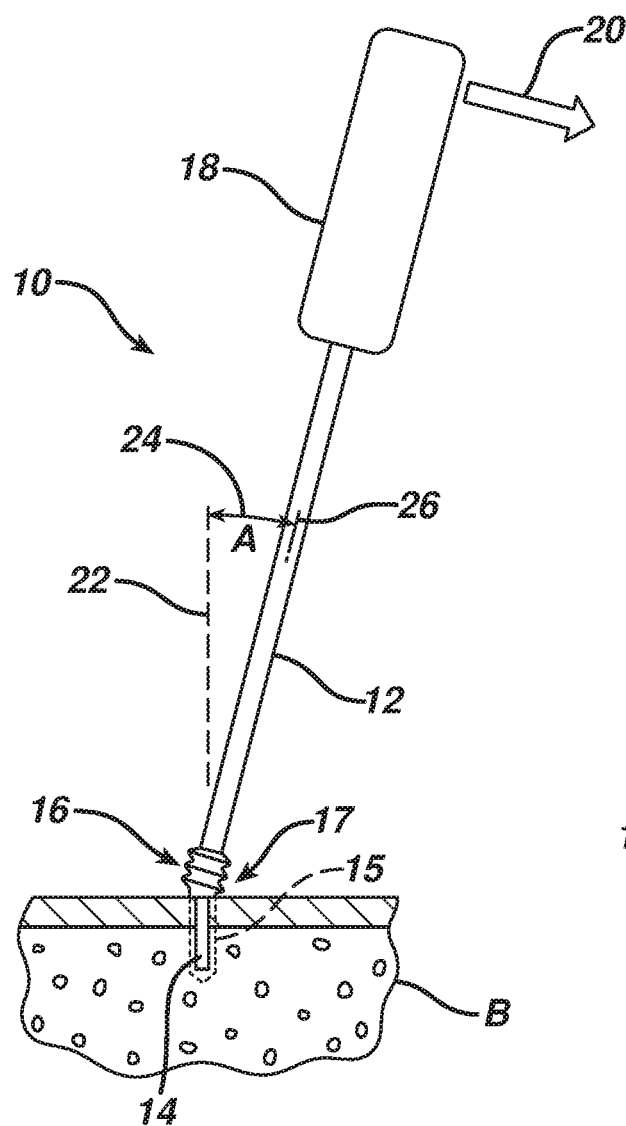
FIG. 1 is a schematic side view of an inserter according to the present invention releasably attached to a suture anchor which has been driven into bone.

FIG. 1 illustrates a compliant inserter 10 according to the present invention having an elongated rigid shaft 12, a substantially rigid tip portion 14, and a compliant region 16. Shaft 12 has a proximal surface including a handle 18 to which an axial and/or rotational driving force is applied. Tip portion 14 is shown substantially within a lumen of a suture anchor 15, illustrated in phantom, that has been driven by inserter 10 into a hole or bore 17 in bone B of a patient.

Shaft 12, with centerline 26, is shown off-axis by an angle A (also indicated as 24) relative to tip portion 14 and anchor 15 in hole 17, represented by bore axis 22. This orientation may be caused by an approach during insertion that is not perpendicular to the axis of the hole 17 in bone B, or by lateral force, represented by arrow 20, applied to handle 18. It is desirable to accommodate misalignment during insertion of up to thirty degrees off-axis.

Figure 2:
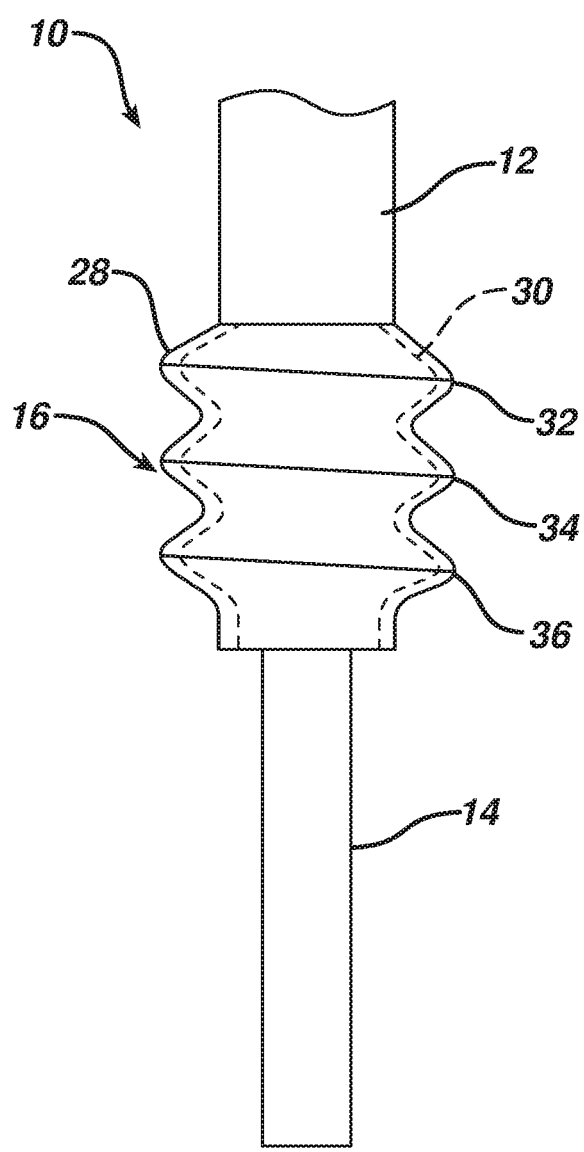
FIG. 2 is an enlarged view of a portion of the inserter of FIG. 1 featuring a bellows-type compliant region.

Compliant region 16 is shown in greater detail in FIG. 2 in an unstressed, axially-aligned condition relative to shaft 12 and tip portion 14. Compliant region 16 serves as a flexure between shaft 12 and tip portion 14 to provide strain relief between these components, that is, it provides greater structural compliance to bending than the other components, especially the tip portion 14, at least when tip portion 14 has been placed within an implant to be inserted. In this construction, compliant region 16 is a hollow bellows 28 which includes a series of convolutions 32, 34 and 36. Inner bellows wall 30 is shown in phantom.

In some constructions, bellows 28 is a cylindrical symmetrical metal bellows such as a sylphon formed by metal spinning onto a mandrel or by hydrostatic forming within a mold. In other constructions, the compliant region is an asymmetric bellows or other structure, and includes corrugations and other variations in cross-sectional shapes to provide a region that bends or otherwise yields more readily than does the tip portion 14 of the inserter 10, at least when tip portion 14 has been placed within an implant to be inserted. Corrugations, channels or other structures may be helical, parallel or with variable skew in orientation. Corrugations and other structures may be circular, oval or polygonal cross-section, or any combination thereof. In one construction, the compliant region includes a helical spring-type element.

In certain constructions, compliant region 16 transmits torque in at least one rotational direction to enable a helically threaded anchor to be driven into bone. Anchor 15 has a hexagonal cross-sectional shape in one construction, such as disclosed by Cauldwell et al. in U.S. Patent Publication No. 2008/0147063. Suitable implant materials include those disclosed by Cauldwell et al. and in U.S. Pat. No. 7,381,213 by Lizardi, both of which are incorporated herein by reference in their entireties.

Figure 3:
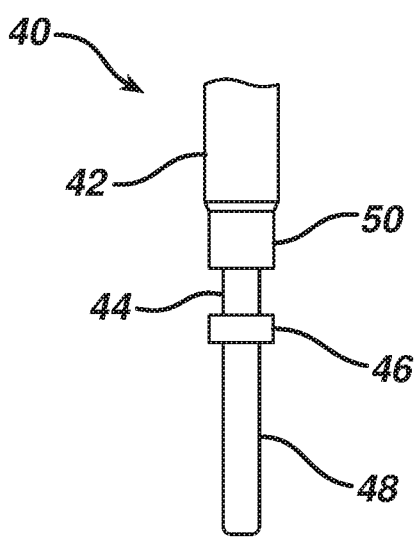
FIG. 3 is a side view of an alternative inserter according to the present invention having a reduced-diameter neck region.
Figure 4:
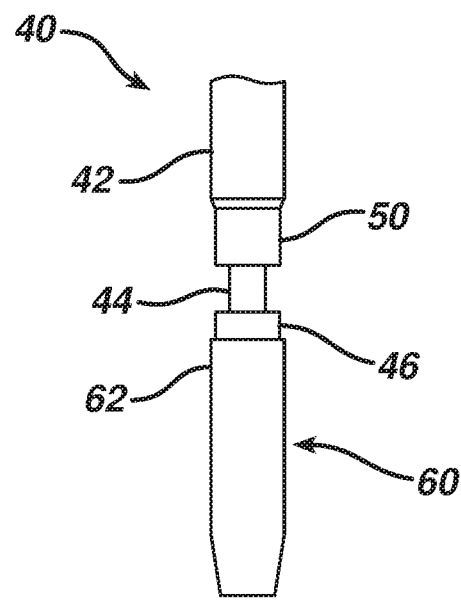
FIG. 4 shows the inserter of FIG. 3 internally supporting a suture anchor.

An alternative inserter 40 is shown in FIGS. 3 and 4 having a shaft 42, a compliant region 44 formed by a reduced-diameter neck, a shoulder 46, and a tip portion 48. The shoulder 46 is shown in FIG. 4 abutting the proximal end 62 of anchor 60, with tip portion 48 fully occupying a lumen within anchor 60. The proximal end of shaft 42 is not illustrated.

In this construction, all components are hollow metal cylinders with a central lumen extending therethrough, and shaft 42 has a transition region 50 which is approximately the diameter of shoulder 46. Tip portion 48 has a wall thickness of 0.006 inches and neck 44 has a length of 2 millimeters and a wall thickness the same or slightly greater than that of tip portion 48, preferably about 0.010 inches. A currently preferred material for neck 44 and tip portion 48 is stainless steel 304 annealed. A suitable material for shaft 42 is stainless steel 17-4 hardened to H900.

Although neck 44 may appear to be less bendable than tip portion 48 when inserter 40 is viewed alone as shown in FIG. 3, the relative lengths, wall thicknesses and materials of inserter 40 are selected relative to dimensions and material of a chosen implant to ensure that bending will first occur along the length of neck 44 when the implant has been combined with, that is, assembled with, the inserter 40, while still providing sufficient columnar strength to transfer enough force to drive the implant into bone. Thus, when tip portion 48 has been placed within an implant lumen, preferably substantially along its entire length, and more preferably fully placed such that shoulder 46 abuts a feature on the implant such as proximal end 62 of suture anchor 60, FIG. 4, the combination of tip portion 48 and the implant provide mutual support and reinforcement during insertion into bone.

Preferably, compliant region 44 provides a flexible bending zone and reduces the rigidity of the inserter against side loading during hammering of shaft 42 to drive anchor 60 into bone. Typical glenoid bone has a hardness of 55-D. It is desirable to have the compliant region 44 yield before the anchor or the bone become damaged. In other constructions, compliant region 44 is formed of a more malleable material, with dimensions adjusted to deliver the performance characteristics described above.

Figure 5:
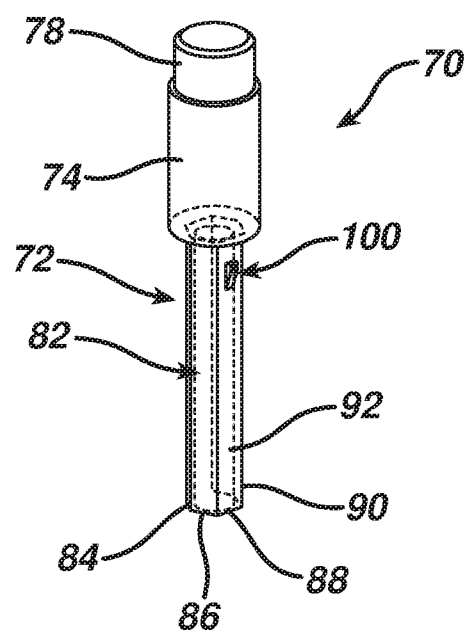
FIG. 5 is a schematic perspective view of yet another inserter according to the present invention having an anchor retention element.
Figure 6:
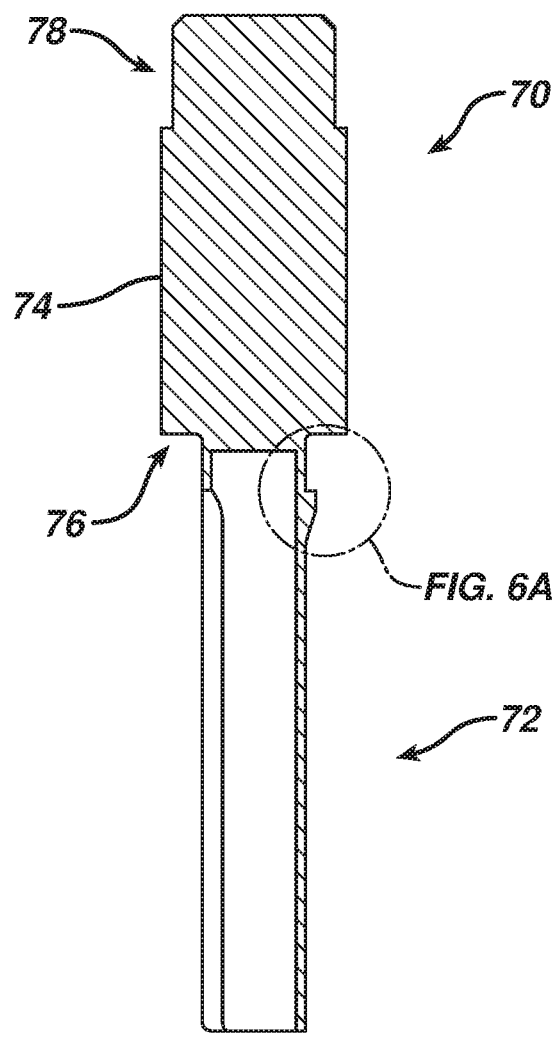
FIG. 6 is an enlarged cross-sectional view of the inserter of FIG. 5.

A distal portion of another inserter 70 according to the present invention is shown in FIGS. 5 and 6 having a tip portion 72 attached to a cylinder 74 with a shoulder 76. Cylinder 74 and a reduced-diameter portion 78 are shown as solid but may be cannulated in other constructions. Also, portion 78 may define an internal socket or external threads to mate with an elongated drive shaft. Portion 78 serves as a compliant region in one construction and, in another construction, a separate, more bendable element is connected to serve as the compliant region.

Tip portion 72 defines an opening 82 and faces 84, 86, 88, 90 and 92 for engaging corresponding features within the lumen of an implant. In other constructions, opening 82 is a solid face so that tip 72 defines a hexagonal shape or other polygon in cross-section.

Figure 6A:
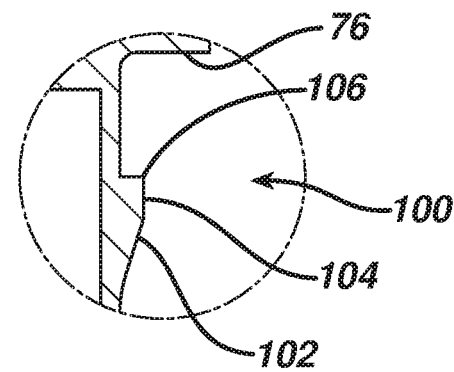
FIG. 6A is an enlarged view of a portion of FIG. 6.
Figure 7:
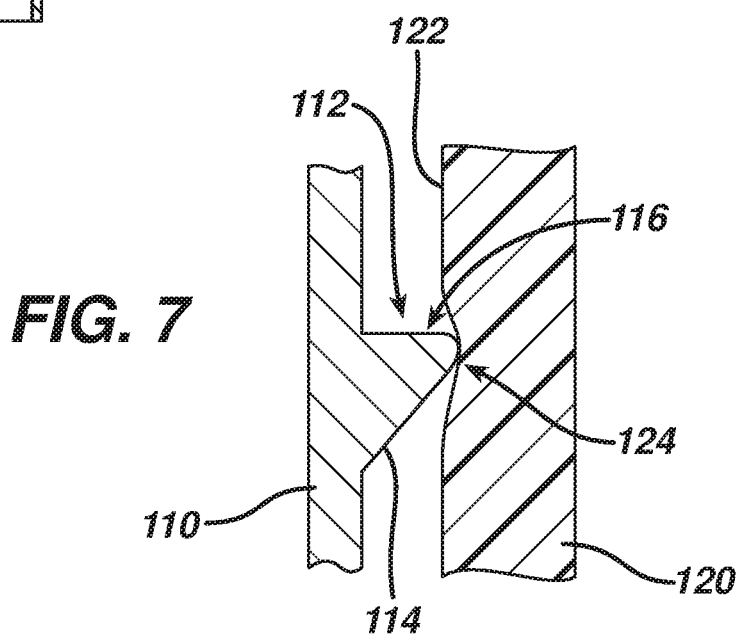
FIG. 7 is a schematic cross-sectional view of an anchor retention element interacting with an internal wall of an implant.

Tip portion 72 further defines an implant retention element 100 which is shown enlarged in FIG. 6A as a projection having a smooth leading distal edge 102, a facet 104, and a sharply-defined transition 106 at a trailing edge. Similarly, FIG. 7 is a schematic cross-sectional view of a barb-like anchor retention element 112 of a tip portion 110 interacting with an internal wall 122 of an implant 120. Features 100 and 112 are examples of one or more possible additions to the distal tip portions of the inserters of FIGS. 1 and 3.

As shown in FIG. 7, barb 112 is of sufficient height to provide an interference fit against the inside wall 122 of the implant 120. Preferably, tip portion 110 and barb 112 are constructed with high stiffness in comparison to the implant 120. In response to the interference fit of the two objects, the implant 120 deforms, preferably elastically, as shown by deformation 124 in the vicinity of barb 112. A smooth lead-in, such as for leading edge 102, FIG. 6A, and leading edge 114, FIG. 7, permits releasable joining of tip portion 110 and implant 120 without skiving or plastic deformation of implant 120. Frictional reaction loading between tip portion 110 and implant 120 is increased by element 112 to minimize unintended separation. Further, the sharp transition edge 106, FIG. 6A, and edge 116, FIG. 7, "bites" into wall 122 at deformation 124 to further resist separation.

After implant 120 is fully installed into bone or other hard substrate, a user of the inserter must provide sufficient proximally-directed withdrawal force on tip portion 110 to overcome frictional resistance and any resistance to shear imparted from implant 120 onto element 112. Preferably, the withdrawal force is less than the force required to separate implant 120 from its substrate or to reduce the fixation between the implant 120 and the substrate. The geometric dimensions and tolerances of elements 100 and 112 may be tailored as desired to optimize these factors.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method of inserting a suture anchor into bone, comprising:
    selecting a suture anchor having a distal end and a proximal end, and defining a lumen open at the proximal end;
    coupling the suture anchor to an inserter including an elongated, substantially rigid shaft having a proximal surface which is capable of receiving a driving force, a substantially rigid tip portion having a distal end and a proximal end, and at least the distal end capable of being placed within the lumen of the suture anchor to provide internal support for the suture anchor during insertion into bone, the inserter further including a distal-facing shoulder at the proximal end of the tip portion capable of engaging the proximal end of the suture anchor, and a compliant region disposed between the shoulder and the shaft which requires less lateral force to bend than the tip portion, at least when the tip portion has been placed within the suture anchor; and
    driving the suture anchor into the bone.

2. The method of claim 1 further including maintaining sterility of the suture anchor and the inserter until the suture anchor is inserted into the bone.

3. The method of claim 1 further including forming a hole in the bone to receive the suture anchor.

* * * * *